(12) United States Patent
Walling et al.

(10) Patent No.: US 9,586,042 B2
(45) Date of Patent: *Mar. 7, 2017

(54) CAP FOR AN IMPLANTABLE ELECTRICAL LEAD ASSEMBLY

(71) Applicants: Grahame Walling, Dee Why (AU); Anthony Paul Burch, Macquarie University (AU); Adrian Cryer, Pymble (AU); Zoran Milijasevic, Bayview Heights (AU)

(72) Inventors: Grahame Walling, Dee Why (AU); Anthony Paul Burch, Macquarie University (AU); Adrian Cryer, Pymble (AU); Zoran Milijasevic, Bayview Heights (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/710,348

(22) Filed: May 12, 2015

(65) Prior Publication Data

US 2015/0343207 A1 Dec. 3, 2015

Related U.S. Application Data

(63) Continuation of application No. 13/403,235, filed on Feb. 23, 2012, now Pat. No. 9,037,231.

(51) Int. Cl.
*A61N 1/00* (2006.01)
*A61N 1/08* (2006.01)
*A61N 1/05* (2006.01)

(52) U.S. Cl.
CPC ............. *A61N 1/08* (2013.01); *A61N 1/05* (2013.01); *A61B 2090/0809* (2016.02); *A61N 1/0541* (2013.01); *A61N 1/0568* (2013.01); *A61N 2001/083* (2013.01)

(58) Field of Classification Search
CPC .................................... A61N 1/08; A61N 1/05
USPC ..................................................... 607/2, 116
See application file for complete search history.

(56) References Cited

U.S. PATENT DOCUMENTS

| 9,037,231 | B2 | 5/2015 | Walling et al. | |
| 2005/0090884 | A1* | 4/2005 | Honeck .................. | A61N 1/057 607/116 |
| 2013/0226254 | A1* | 8/2013 | Walling ................... | A61N 1/05 607/2 |

* cited by examiner

*Primary Examiner* — Edward Moran
*Assistant Examiner* — Nadia A Mahmood

(57) ABSTRACT

A cap for an implantable medical device electrical connector lead assembly and methods of use. A cap for protecting an electrical connector lead assembly of an implantable medical device is disclosed. The cap includes a body defined by a mating surface and a non-mating surface. The mating surface is adapted for electrically insulating engagement with an electrical connector lead assembly of an implantable medical device. The cap includes a body having a mating surface and an electrical network disposed therein. The electrical network includes first and second contacts exposed at the mating surface, a first circuit element, and two conductive pathways connecting the contacts to the circuit element. The body is configured to mate with the electrical connector lead assembly such that each contact conductively engages a corresponding contact of the electrical connector lead assembly when the cap and electrical connector lead assembly are mated.

25 Claims, 16 Drawing Sheets

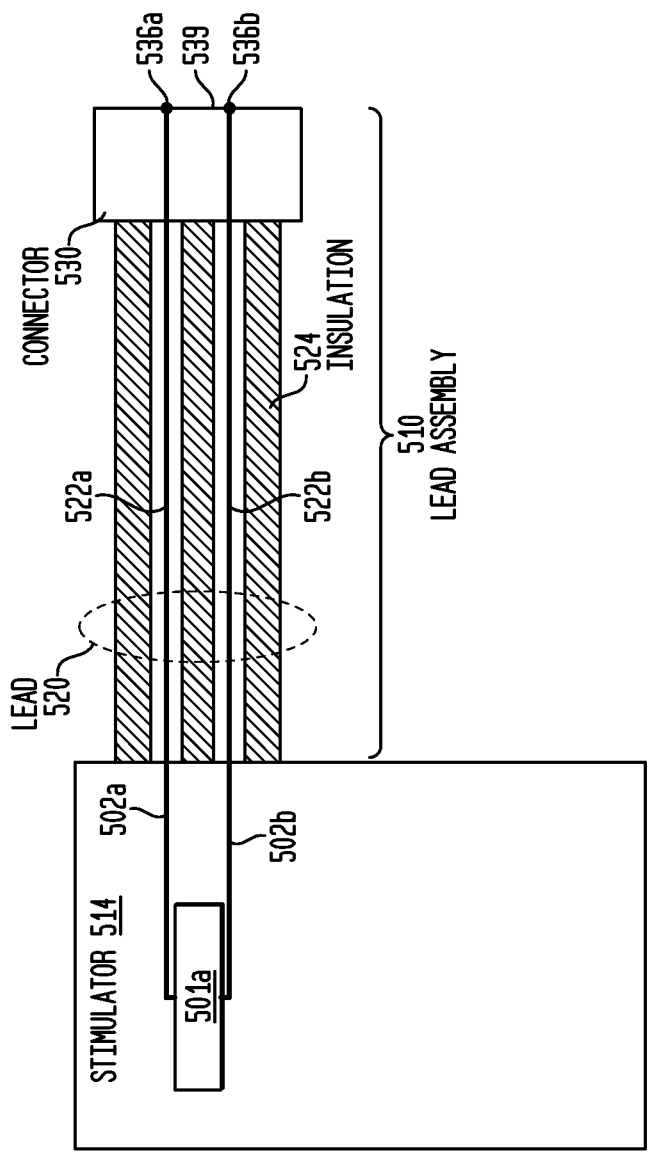

CAP FOR AN IMPLANTABLE ELECTRICAL LEAD ASSEMBLY

CROSS REFERENCE TO RELATED APPLICATIONS

This application is a continuation of U.S. application Ser. No. 13/403,235, filed Feb. 23, 2012, the disclosure of which is hereby incorporated by reference herein in its entirety.

BACKGROUND

Field of the Invention

The present invention relates generally to implantable electrical leads, and more particularly, to a cap for an implantable electrical lead assembly.

Related Art

Devices that have one or more components designed for temporary or permanent implantation in a recipient provide numerous therapeutic and/or other benefits. Examples of such implantable medical devices include implantable medical devices such as cardiac assist devices, pacemakers, hearing prostheses, drug delivery devices, monitoring systems, and so on. Oftentimes, implantable medical devices have multiple implantable components. Typically, the implantable components are connected to each other electrical lead assemblies suitable for transferring data, instructions, programs and other information, as well as power, between the implanted components.

Some implantable medical devices are designed to be arranged in different configurations, with some configurations having a different combination of implantable components. The implemented configuration of such implantable medical devices may change over time as the treated condition or desired functionality changes. Other implantable medical devices are designed to accept new implantable components in the future. As such, it is not uncommon for implantable medical devices to include implantable components which have one or more electrical lead assemblies that are not connected to another implantable component at time of surgery. Such electrical lead assemblies may be associated with an unused configuration or may be provided to facilitate incorporation of a new component in the future.

SUMMARY

In accordance with aspects of the present invention, a cap for protecting an electrical connector lead assembly of an implantable medical device is disclosed. The cap includes a body defined by a mating surface and a non-mating surface. The mating surface is adapted for electrically insulating engagement with an electrical connector lead assembly of an implantable medical device.

In accordance with one aspect of the present invention a cap for an implantable medical device electrical connector lead assembly is disclosed. The cap includes a body having a mating surface and an electrical network disposed therein. The electrical network includes first and second contacts exposed at the mating surface, a first circuit element, and two conductive pathways connecting the contacts to the circuit element. The body is configured to mate with the electrical connector lead assembly such that each contact conductively engages a corresponding contact of the electrical connector lead assembly when the cap and electrical connector lead assembly are mated.

In accordance with another aspect of the present invention methods of assessing the integrity of a capped electrical connector lead assembly of an implanted device are disclosed. The cap includes a first circuit element connected across conductive pathways of the electrical connector lead assembly. In such methods, a voltage is applied across the conductive pathways of the implanted electrical connector lead assembly. A characteristic, e.g., impedance, of the network across the conductive pathways is measured. The measured characteristic is compared to an expected value of the network characteristic, e.g., the impedance of the first circuit element in typical cases where the impedance of the electrical connector lead assembly is negligible.

In accordance with a further aspect of the present invention methods of using a magnetic location module to locate an electrical connector lead assembly of an implanted device that is terminated with a cap are disclosed. The cap includes an electromagnetic induction coil connected across conductive pathways of the connector lead assembly. In such methods, the magnetic induction coil is energized through the conductive pathways of the connector lead assembly. A magnetic field is generated in the magnetic location module. The magnetic location module is moved in proximity to a suspected location of the cap. The location of maximum magnetic coupling between the magnetic location module and the energized electromagnetic induction coil is determined.

BRIEF DESCRIPTION OF THE DRAWINGS

Embodiments of the disclosed technology are described below with reference to the attached drawings, in which:

FIG. 5 is a schematic view of an embodiment of the implanted component of FIG. 2, depicting an electrical connector lead assembly of the implanted component;

DETAILED DESCRIPTION

Aspects of the present invention are generally directed to a cap for an electrical lead assembly of an implantable medical device (IMD), and methods of using the cap for lead integrity testing, for locating the connector lead assembly, and for communicating with the IMD.

In some embodiments, the cap includes a body in which an electrical network is disposed, the electrical network comprising first and second contacts, a first circuit element, and two conductive pathways connecting the contacts to the circuit element. The body is configured to mate with the connector lead assembly. The contacts are disposed proximate to or on a mating surface of the cap such that each contact conductively engages a corresponding contact of the connector lead assembly when the cap and connector lead assembly are mated. In some embodiments, the electrical network further comprises a second circuit element series-connected to the first circuit element, and a conductive plate conductively exposed to the exterior of the cap and electrically connected to a conductive path between the series-connected circuit elements.

Further, embodiments of the cap may be used to assess the integrity of the lead assembly of an implanted device. Once the lead assembly is capped with a cap of the present invention, a voltage is applied across the conductive pathways of the lead assembly. A characteristic, e.g., impedance, of the network across the conductive pathways can be measured. The measured characteristic is compared to an expected value of the network characteristic, e.g., the impedance of the cap circuit element, since the impedance of the connector lead assembly is typically negligible in most arrangements Further, embodiments of the above cap may be used to locate a connector lead assembly. In some embodiments, the cap includes a magnetic induction coil that can be energized through the conductive pathways of the lead assembly. A magnetic field is generated in a magnetic location module. In use, the magnetic location module is moved over the skin of the recipient. When it is proximate to the cap, an induction coil in the location module becomes magnetically coupled to the induction coil in the cap. The location of maximum magnetic coupling between the magnetic location module and the magnetic induction coil is determined as the location of the cap.

Aspects and embodiments of the present invention, while finding utility in connection with any type of implantable electrical lead, are described herein in the context of electrical lead assemblies commonly used in cochlear implants.

Figure 1:
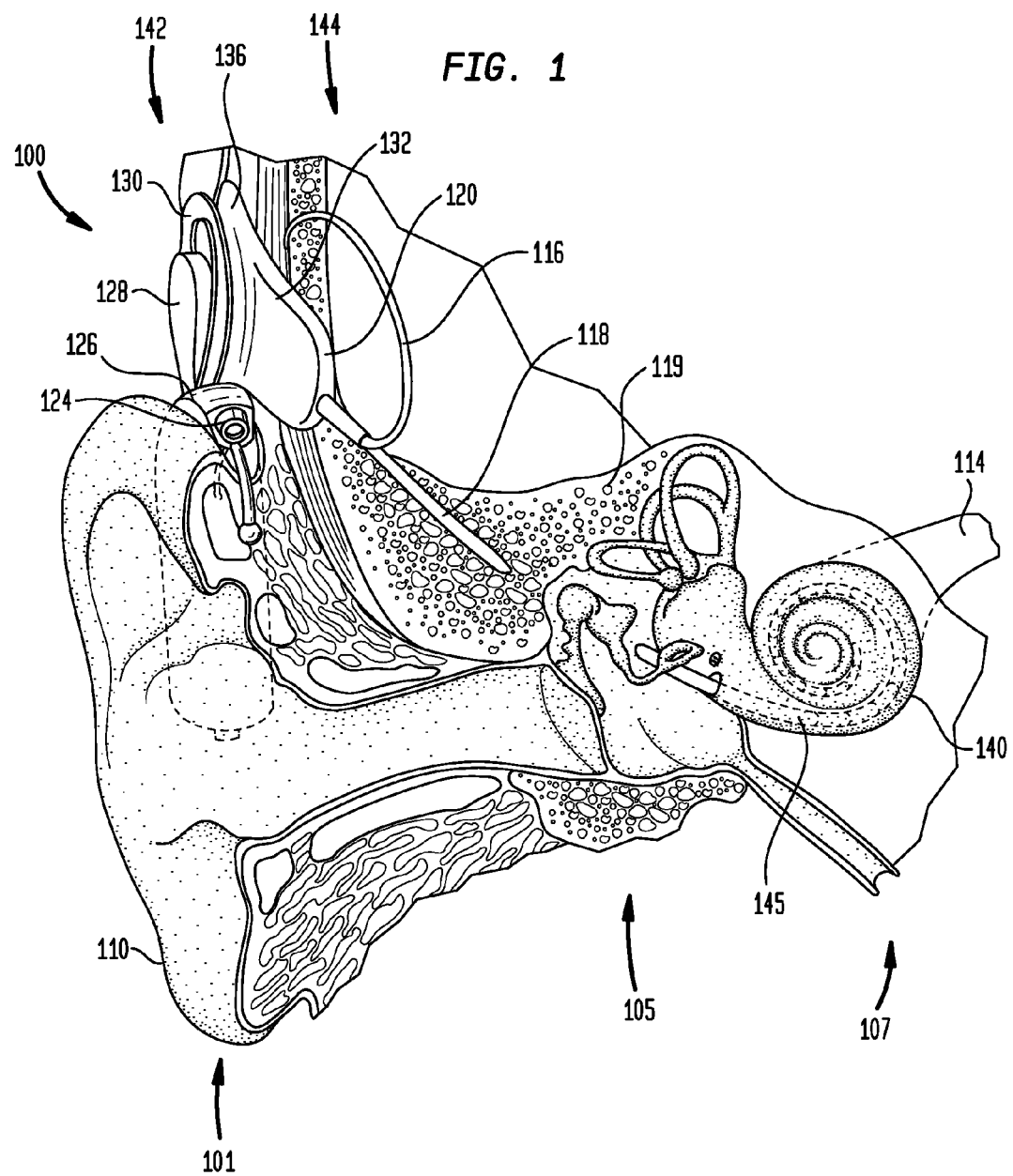
FIG. 1 is a perspective view of an exemplary implantable medical device, namely an implantable medical device commonly referred to as a cochlear implant, which in connection with embodiments of the present invention may be advantageously implemented.

FIG. 1 is a perspective view of an exemplary cochlear implant 100 implanted in a recipient having an outer ear 101, a middle ear 105, and an inner ear 107. Cochlear implant 100 comprises an external component 142 that may be directly or indirectly attached to the body of the recipient, and an internal or implantable component 144 that may be temporarily or permanently implanted in the recipient.

External component 142 typically comprises one or more sound input elements, such as microphone 124 for detecting sound, a sound processing unit 126, a power source (not shown), and an external transmitter unit 128. Sound processing unit 126 processes the output of microphone 124 that is positioned, in FIG. 1, by auricle 110 of the recipient. Sound processing unit 126 generates encoded signals that are provided to external transmitter unit 128.

Internal component 144 comprises an internal receiver unit 136, a stimulator unit 132, an elongate stimulating lead assembly 118, and a connector lead assembly 116 for connecting to other implantable components. Internal receiver unit 136 and stimulator unit 132 are hermetically sealed within a biocompatible housing, sometimes collectively referred to as a stimulator/receiver unit 120. Internal receiver unit 136 comprises an internal coil 136 that receives power and stimulation data from external coil 130. Elongate stimulating lead assembly 118 has a proximal end connected to stimulator/receiver unit 120, and extends through mastoid bone 119. Lead assembly 118 has a distal region, referred to as electrode assembly 145, implanted in cochlea 140. Stimulator unit 132 generates stimulation signals that are applied by electrode assembly 145 to cochlea 140, thereby stimulating auditory nerve 114.

Figure 2:
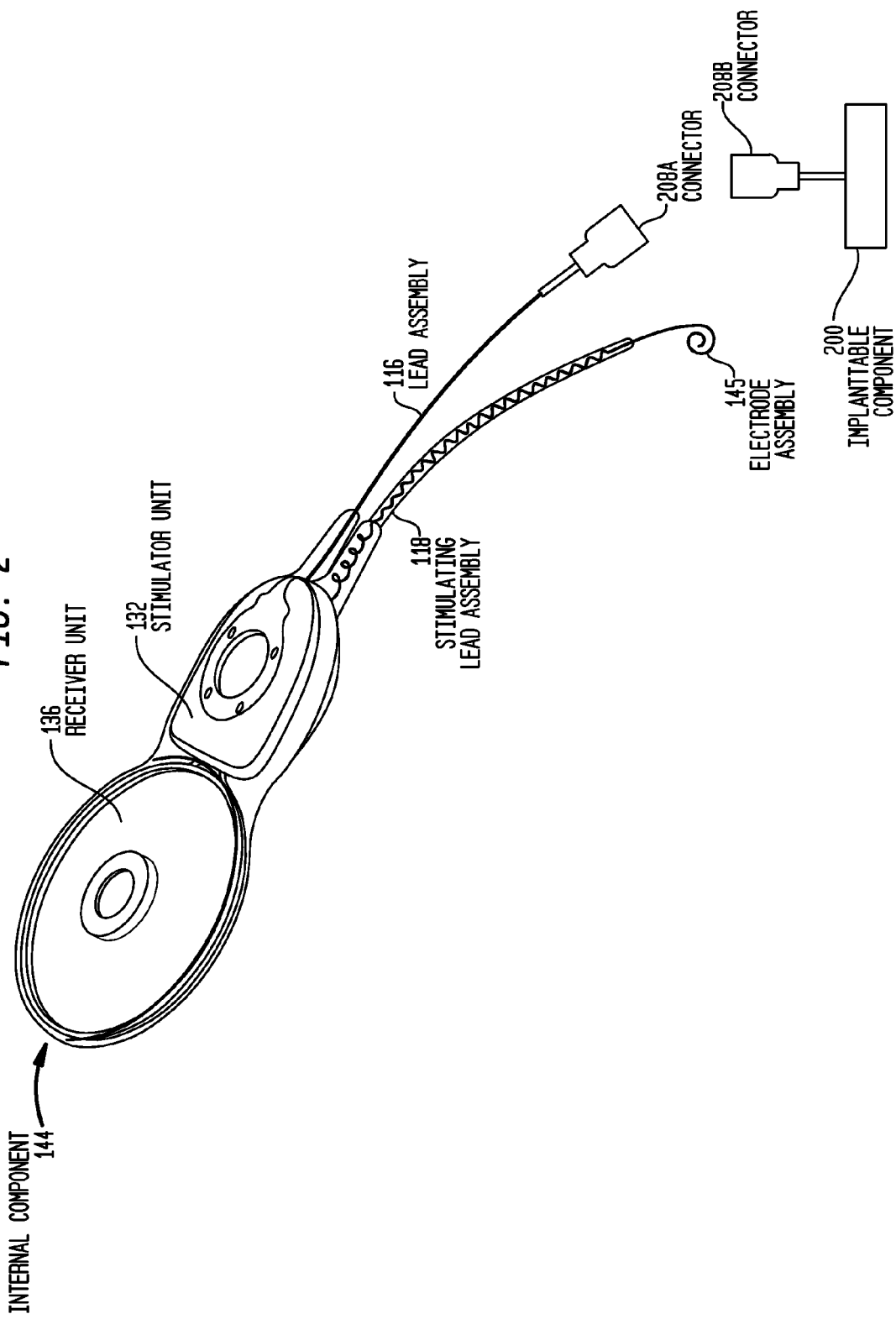
FIG. 2 is a perspective view of an embodiment of the cochlear implant internal component illustrated in FIG. 1, depicting the lead assemblies.
Figure 3A:
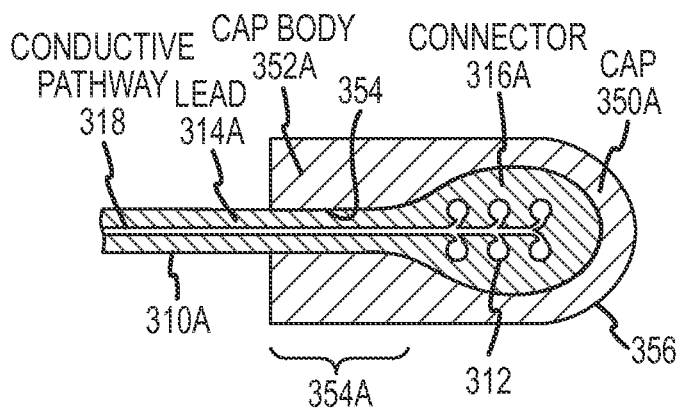
FIGS. 3A-3D illustrate four example lead assemblies, each with a cap (shown in cross section) in accordance with the present technology.
Figure 3B:
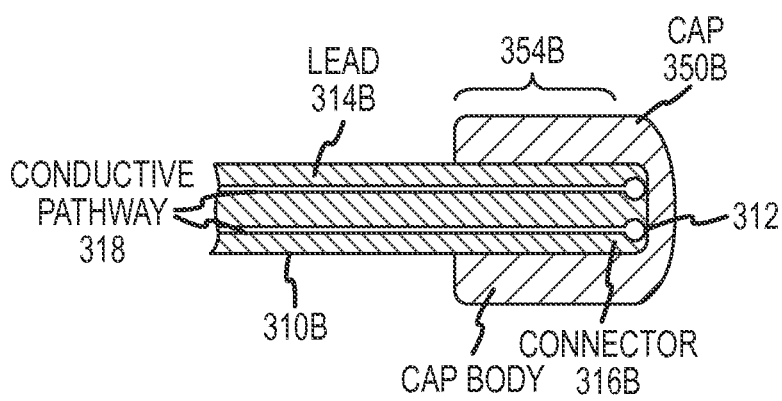
Figure 3C:
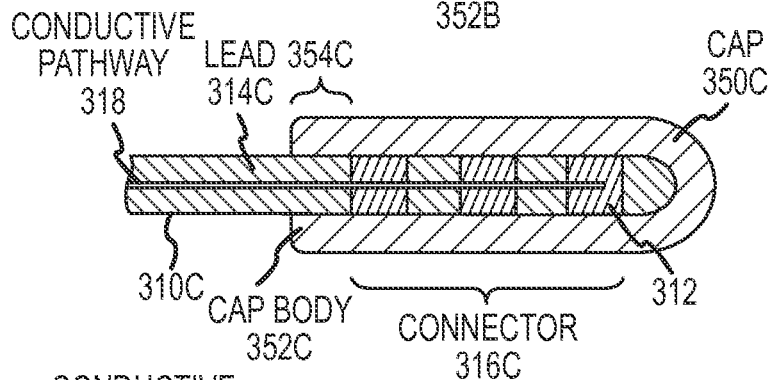
Figure 3D:
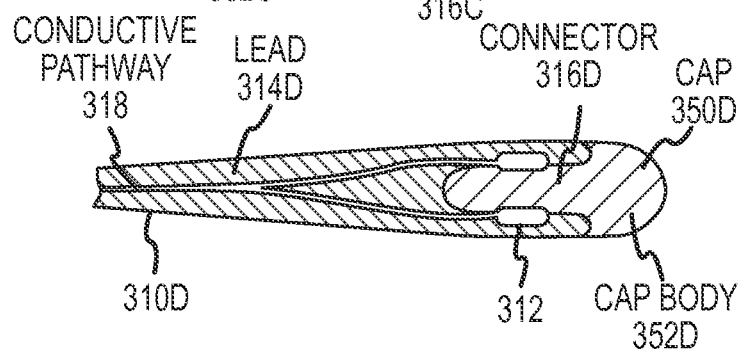

FIG. 2 is a perspective view of an embodiment of internal component 144 illustrated in FIG. 1. As noted, internal component 144 comprises a receiver unit 136, a stimulator unit 132 and two lead assemblies 116 and 118. Connector lead assembly 116 is configured to connect internal component 144 to a separate implantable component. To this end, the second lead, lead assembly 116 includes an electrical connector 208A that mates with a connector 208B of a separate module. The separate module can be, for example, a microphone or other sound transducer, a power source, and/or a speech processor.

In this exemplary application, use of connector lead assembly 116 is optional. If not used in a particular recipient at the time of initial implantation, lead assembly 116 remains dormant in the recipient until it is used in the future. Prior to such subsequent use, connector lead assembly 116 may be damaged or may migrate to an unknown location in the recipient. Also, the lead or connector may be damaged at any time prior to or during surgical implantation. Even without migration of the connector lead assembly, the location of the interface may not be known at the time of the upgrade.

In some embodiments, during the period of use of the implant, an unused connector is terminated with a cap. FIGS. 3A-3D are cross-sectional views of four exemplary lead assemblies 310A-D, each having a lead 314A-D and connector 316A-D, respectively. A cap 350A-D, respectively, is mated to connector 316A-D. Lead assembly 310A terminates in a paddle connector 316A having six (6) contacts 312, while connectors 316B and 316C each have two contacts 312, and connector 316D has two contacts 312. Each contact 312 is electrically connected to a conductive path 318 that traverses the respective lead 314. It should be appreciated that while the each conductive path 318 is electrically insulated from other conductive paths 318 in the same lead 314, in some of the illustrative embodiments, a single conductive path 318 representing the appropriate quantity of conductive paths 318 is depicted in the figure.

Referring to cap 350A as exemplary of caps 350B-D, cap 350A includes a cap body 352 defined by a mating surface 354 and a non-mating surface 356. Cap body 352 can be made of a biocompatible electrically insulating material such as silicone, polyurethane, polyurethane or PTFE, and in some embodiments, is reinforced. In one embodiment, the reinforcement is in cap body 352, and in other embodiments, the reinforcement surrounds the cap body. The reinforcement can include one or more helically wound wires, and the stiffness of the reinforcement can vary along the length of the cap, e.g., by varying the pitch of the helical winding. In some embodiments, the reinforcement is a tube, which can be perforated. The stiffness of the tube can be varied by varying the size and spacing of the perforations. In alternative embodiments, the reinforcement is a patterned mesh, and the stiffness of the patterned mesh can vary along the length of the cap. Suitable materials for reinforcement include polymers or metals such as polyurethane, titanium, platinum, iridium or gold.

Cap mating surface 354 is adapted to create an electrically insulating seal at least at contacts 312 of connector 316. Embodiments of cap body 352 also protect portions of lead 314 adjacent to connector 316. For example, cap bodies 352A-C each has an elongate section 354A-C that define an elongate volume for receiving (not necessarily in electrically insulatingly sealing engagement) a portion of lead 314A-C, respectively. Depending on the anticipated environment and cap embodiment, protection includes any combination of protection from fluid ingress, tissue growth, mechanical damage (which can be done with a scalpel, a needle, or other sharp object).

Figure 4A:
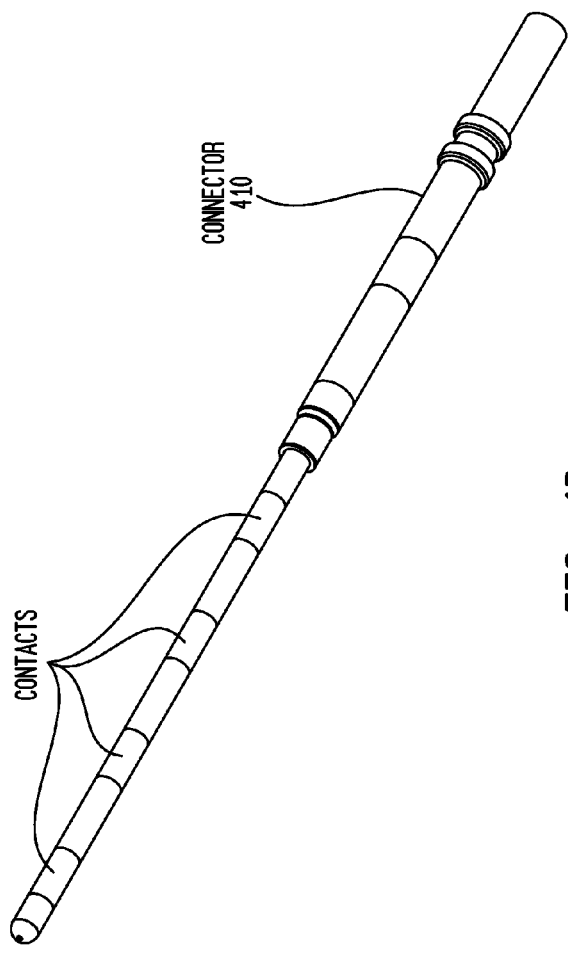
FIGS. 4A and 4B are perspective views of a four-electrode male connector and a cap for the connector in accordance with the present technology.
Figure 4B:
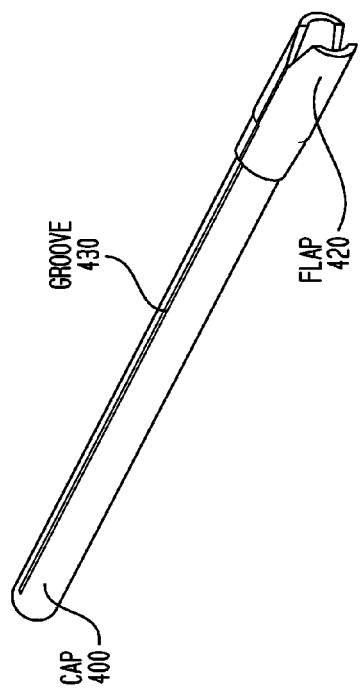

FIGS. 4A-4B are perspective views of a cap 400 and a four-electrode male connector 410. In this illustrative embodiment, cap 400 includes removal features. A first removal feature is shown as flap 420 for gripping and tearing the cap 400. A second removal feature is a weakened region, shown as a groove 430 on the outside of cap 400. Groove 430 can be placed on the inside of cap 400. In some embodiments, a filament (not shown), e.g., a thread or a wire, can be run along the weakened region. One or both ends of the filament can be left top protrude out of the cap. Such an end can be grasped, e.g., by fingertips or an instrument, and pulled, severing the cap and either releasing or weakening it. Both a filament and a groove can be used in conjunction as removal features.

In some embodiments, the cap includes a body in which an electrical network is disposed. The electrical network comprising at least first and second contacts, at least one circuit element, and conductive pathways connecting the contacts to the circuit element. The circuit element(s) include, for example, a conductive pathway, an electrical impedance, and a magnetic induction coil. In some embodiments, the network also includes a conductive plate for contacting the recipient's body. The cap body is configured to mate with the implanted device connector lead assembly. The contacts are disposed on a mating surface of the cap such that each contact conductively engages a corresponding contact of the connector lead assembly when the cap and connector lead assembly are mated. The present technology can facilitate connector lead assembly integrity testing (e.g., short circuit, open circuit, insulation damage), connector lead assembly location, and communication with the implanted device (e.g., for device diagnostics) from outside the recipient. These features can be provided by embodiments of the present technology prior or during surgical intervention, e.g., prior to implanting an upgrade.

FIG. 5 is. a schematic view of a stimulator 514 (representing an implantable medical device) having a connector lead assembly 510. Connector lead assembly 510 includes a lead 520 and a connector 530. Lead 520 includes at least two (2) conductive pathways 522a, 522b separated from each other by insulation 524, and separated from the implantation environment by insulation 524. Connector 530 includes contacts 536a, 536b. Contacts 536 are formed for mating engagement with the contacts of a mating cap, and the contacts of a mating connector. Connector 530 includes an electrically insulating connector body forming a connector mating surface 539 compatible with a corresponding mating surface of each of a connector lead assembly, a cap, and a load. Conductive pathways 522a, 522b can be connected to circuit element 501a, which can be an interface circuit element for connection to, for example, upgrade modules, and can be a test circuit element used in connector lead assembly 510 integrity testing and connector 530 location. Suitable material for the insulating connector body includes biocompatible material such as silicone, PTFE or polyurethane.

While the conductive pathways 502, and 522 are shown schematically as single lines for ease of illustration, actual conductive pathways can be of other types and quantities as known to those of skill in the art. For example, conductive pathways can be co-axial, conductive pathways can be braided, conductive pathways can be twisted, the conductive pathways can be shielded, etc. While insulation 524 is identified by a single reference numeral, insulation 524 can be of different type (e.g., silicone, parylene, PTFE) and quantity between the conductive pathways, and between the conductive pathways and the implantation environment.

Figure 6:
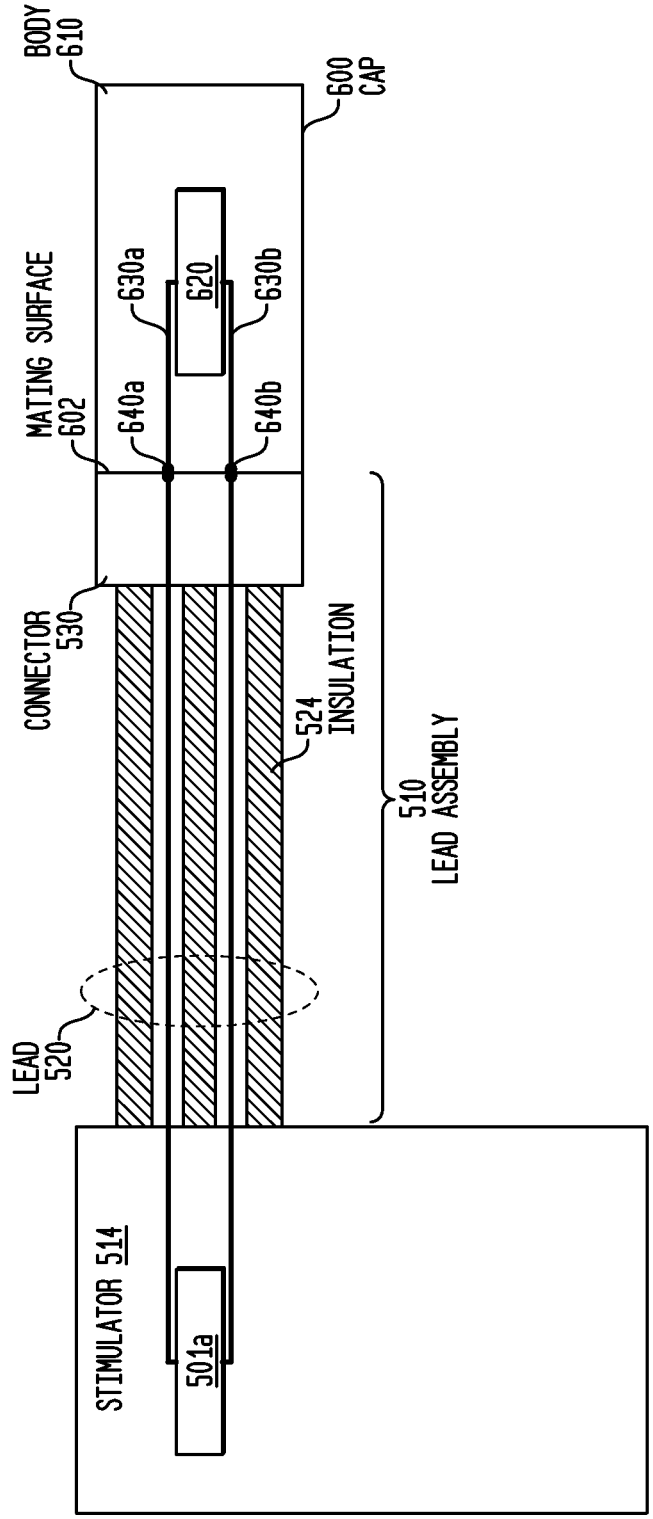
FIG. 6 is a schematic view of embodiments of a cap of the present technology in relation to the implanted component and connector lead assembly of FIG. 5.

FIG. 6 is a schematic view of embodiments of a cap 600 of the present technology in relation to the stimulator unit 514 and connector lead assembly 510 (as distinguished from the stimulating lead assembly 118 of FIG. 1 and FIG. 2) of FIG. 5. Cap 600 includes cap body 610, at least one circuit element 620, and cap conductors 630a, 630b that connected the cap circuit element 620 to cap contacts 640a, 640b. Contacts 640, 640b are formed for mating engagement with contacts of connector lead assembly 510. Cap mating surface 602 is compatible with a corresponding mating surface of a connector lead assembly. Cap circuit element 620 can be characterized by an electrical impedance that can be resistive, capacitive, and inductive. Cap circuit element 620 can be a passive element such as a resistor, capacitor, inductor, and passive antenna; and can be an active element such as a transmitter, receiver, and a transceiver. In each case, cap circuit element 620 enables at least one of testing and location of implanted devices.

In some embodiments, cap 600 includes a drug-doped component, that includes a host material, a drug embedded in the host material, and may further include a sacrificial material integrated with the host material. The sacrificial material can facilitate the release of the embedded drug from the drug-doped component of the cap. The sacrificial material can facilitate the release of the drug from the drug-doped component through the creation of voids in the host material upon dissolution of the sacrificial material upon contact with a solvent. The contact with a solvent can be upon implant of the component in a recipient, e.g., body fluid as the solvent. The host material can be one or more of a polysiloxane and a silicone rubber.

The drug can be one or more of an anti-inflammatory, an antimicrobial, a growth factor, an antibody, an anti-oxidant, an antibiotic, and a corticosteroid. The cap can include a single drug or a combination of two or more drugs, selected from the group consisting of: anti-oxidants (e.g., nitric oxide), antibiotics, anti-inflammatories, immuno-modulators, enzymes or molecules that are known to dissolve or degrade the components of a tissue capsule (e.g. collagenase, thrombin, fibrinolysin, trypsin, hyaluronidase, or a combination thereof), hormones or other analogs (e.g., luteinizing-hormone-releasing hormone, steroids, corticosteroids, growth factors), antibodies (e.g., anti-vascular endothelial growth factor antibodies, tumor necrosis factor inhibitors), cytokines (e.g., α-, -β, or γ-interferons), interleukins (e.g., IL-2, IL-10). In general, the drug can be use for treating, decreasing the risk of, and preventing in whole or in part: infection and biofilm formation, inflammation and fibrotic tissue encapsulation, and tissue integration.

The sacrificial material can be one or more of: a glucose monomer, a sugar, cyclodextrin, a material that is at least one of dissolvable and resorbable in the environment of an implant site, a salt, a bioresorbable material, hyaluronic acid, polyurethane, polyester, polyamide, polyvinyl alcohol, and polyacrylic acid. In some embodiments, the sacrificial material is the host material, and the sacrificial material facilitates the release of the drug from the drug-doped component through changing a property of the sacrificial material. The change in property can be brought about by exposing the drug-doped component to an ethanol wash. For a cap comprising a drug-doped component, the drug doped material can be applied at a distance from conductive pathways. The drug doped material can be a physical feature of the cap, such as a region at or towards the surface. including a ridge or a spine.

Figure 7:
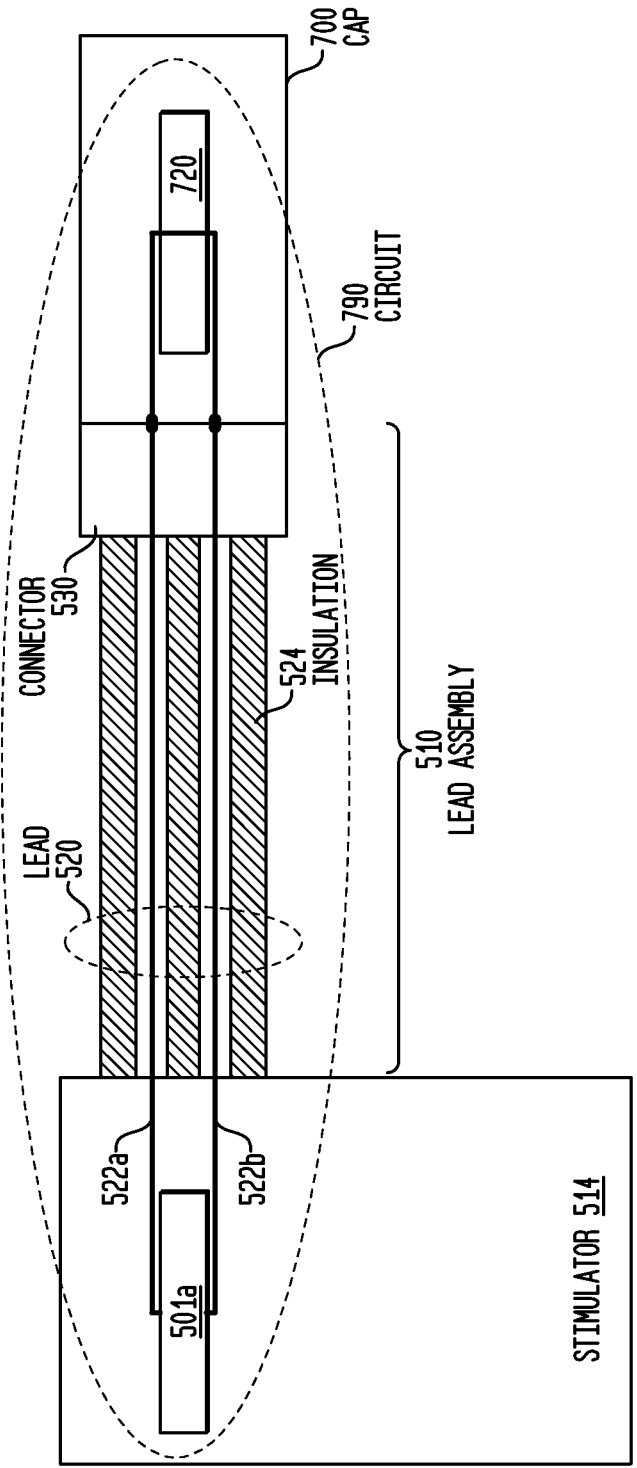
FIG. 7 is a schematic view of embodiments of a cap of the present technology, containing a conductive pathway, in relation to the implanted component and connector lead assembly of FIG. 5.

FIG. 7 is a schematic view of embodiments of a cap 700 of the present technology, containing a conductive pathway circuit element 720 in relation to the stimulator 514 and connector lead assembly 510 of FIG. 5. Conductive pathway 720 can be used to test for open circuits in circuit 790. For example, stimulator 514 can be commanded, e.g. via signals from external coil 130 to internal coil 136, to test the response of circuit 790. Any response that shows a resistance between 522a and 522b above a threshold (with circuit element 501a equal to an open circuit) can be interpreted as indicating an open circuit in circuit 790. Such a result can be taken as indicative of an open circuit in connector lead assembly 510.

Figure 8:
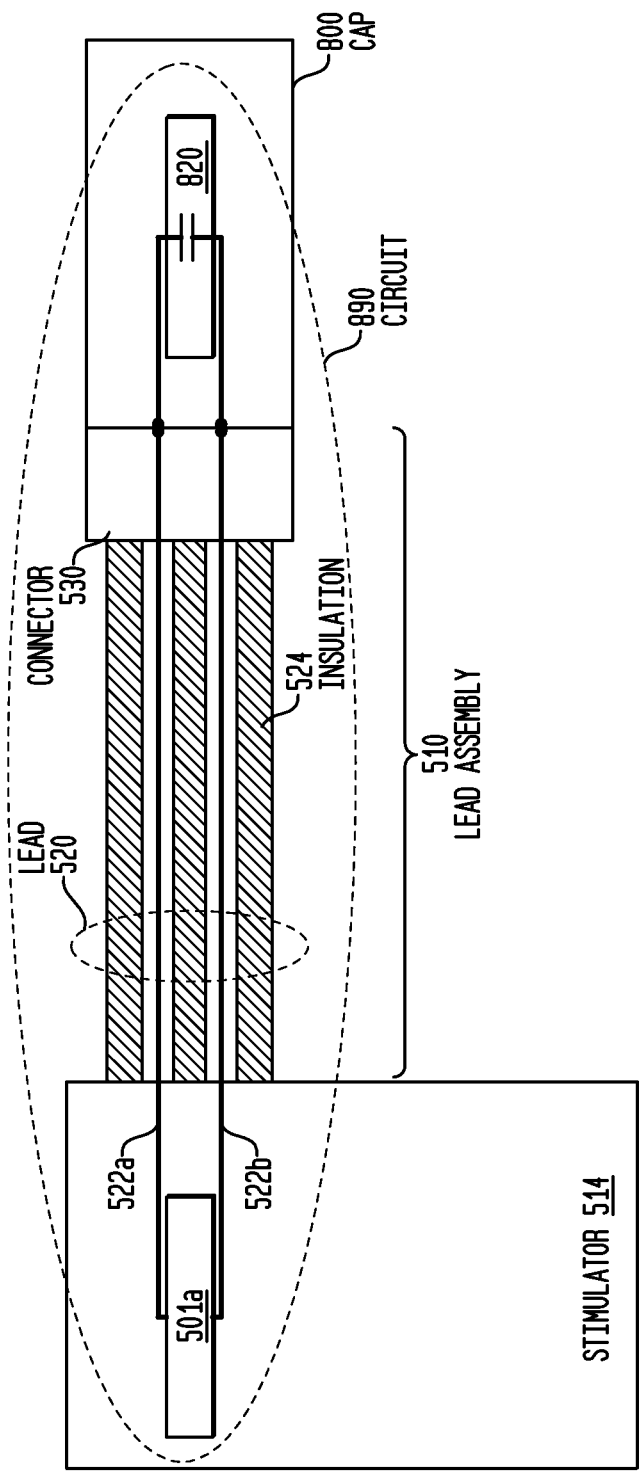
FIG. 8 is a schematic view of embodiments of a cap of the present technology, containing a capacitor, in relation to the implanted component and connector lead assembly of FIG. 5.

FIG. 8 is a schematic view of embodiments of a cap 800 of the present technology, containing a capacitive circuit element 820 in relation to the stimulator 514 and connector lead assembly 510 of FIG. 5. Capacitive circuit element 820 can be used to test for both open circuits and shorts in circuit 890.

For example, stimulator 514 can be commanded, e.g. via signals from external coil 130 to internal coil 136, to test the response of circuit 890 by placing a DC voltage, with minimal or no AC component, across conductive pathways 522a and 522b using circuit element 501a. Any response that shows a current flow in circuit 890 above a threshold under these conditions indicates a short circuit.

As a further example, stimulator 514 can be commanded, e.g. via signals from external coil 130 to internal coil 136, to test the response of circuit 890 by placing a AC voltage, with no DC bias, across conductive pathways 522a and 522b. A response that deviates from the characteristic response of capacitive circuit element 820 can be an indication of an open circuit (no response) or a short circuit (a response with a DC bias).

Figure 9:
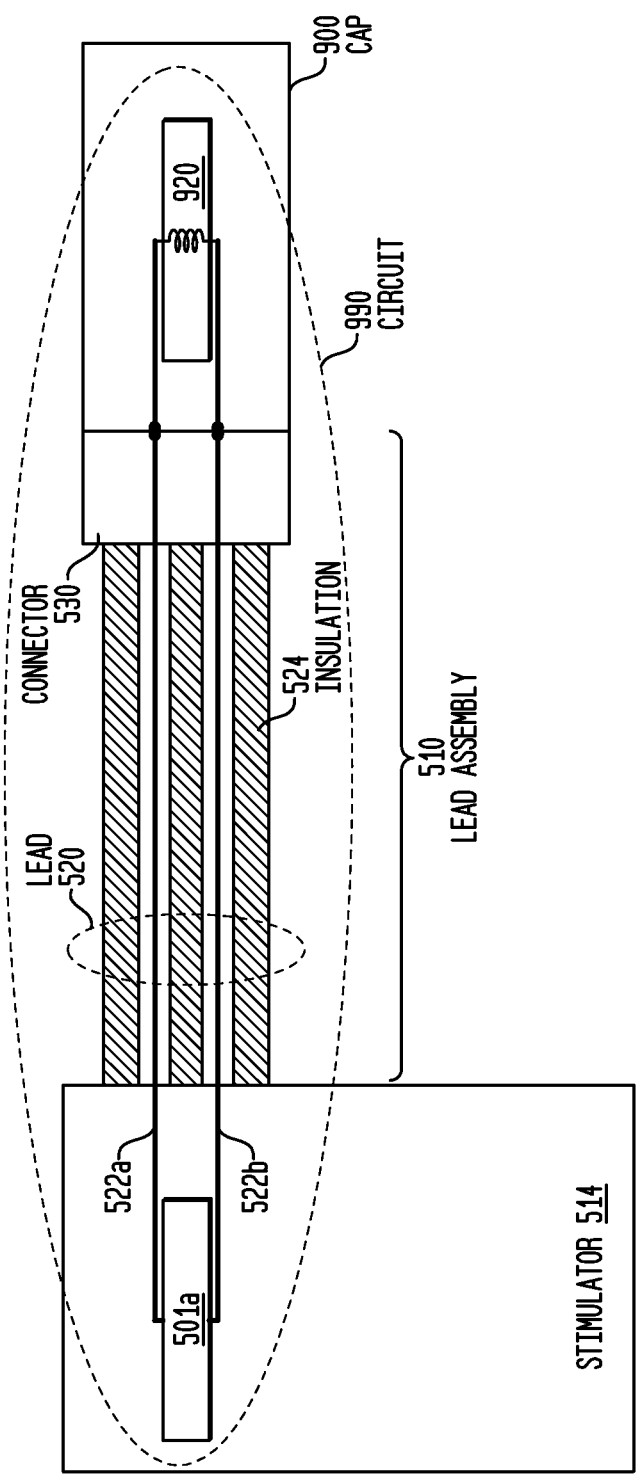
FIG. 9 is a schematic view of embodiments of a cap of the present technology, containing an inductor, in relation to the implanted component and connector lead assembly of FIG. 5.

FIG. 9 is a schematic view of embodiments of a cap 900 of the present technology, containing an inductive circuit element 920 in relation to the stimulator 514 and connector lead assembly 510 of FIG. 5. Inductive circuit element 920 can be used to test for both open circuits and shorts in circuit 690.

For example, stimulator 514 can be commanded, e.g. via signals from external coil 130 to internal coil 136, to test the response of circuit 690 by placing a DC voltage, with minimal or no AC component, across conductive pathways 522a and 522b using circuit element 501a. A response that shows a resistance between 522a and 522b above a threshold (with circuit element 501a equal to an open circuit) can be interpreted as indicating an open circuit in circuit 990. Such a result can be taken as indicative of an open circuit in connector lead assembly 510.

As a further example, stimulator 514 can be commanded, e.g. via signals from external coil 130 to internal coil 136, to test the response of circuit 990 by placing a AC voltage, with no DC bias, across conductive pathways 522a and 522b using circuit element 501a. A response that deviates from the characteristic response of inductive circuit element 920 can be an indication of an open circuit (no response) or a short circuit (a response with a DC bias).

Figure 10:
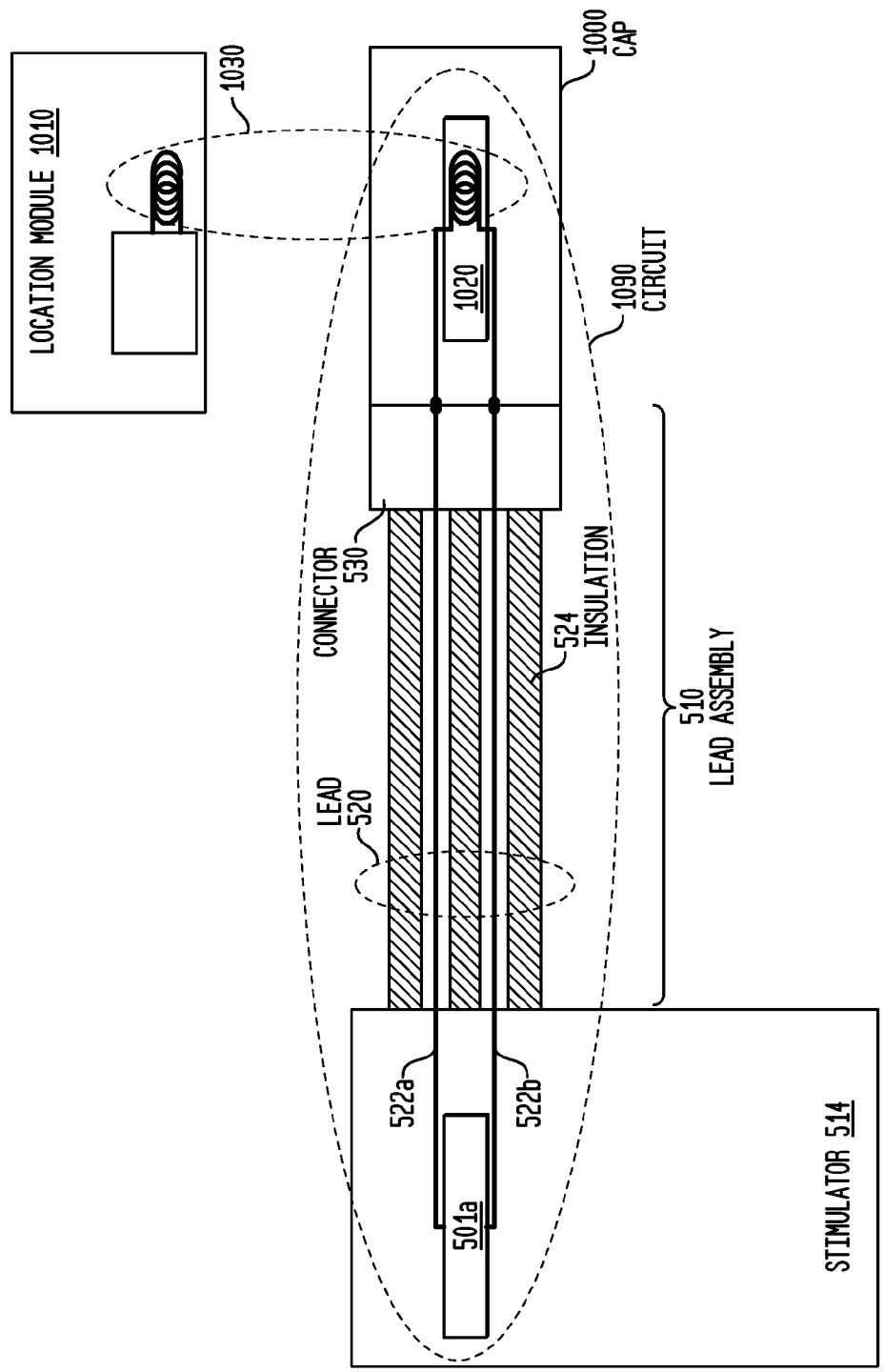
FIG. 10 is a schematic view of embodiments of a cap of the present technology, containing a magnetic induction coil, in relation to the implanted component and connector lead assembly of FIG. 5.

FIG. 10 is a schematic view of embodiments of a cap 1000 of the present technology, containing a magnetic induction coil 1020 in relation to the stimulator 514 and connector lead assembly 510 of FIG. 5. Magnetic induction coil 1020 can be used to locate cap 1000, and by extension locate connector 530.

For example, stimulator 514 can be commanded, e.g. via signals from external coil 130 to internal coil 136, to power circuit 1090. Location module 1010 can be used to determine the location of cap 1000 through determining the point of maximum magnetic coupling between location module 1010 and powered magnetic induction coil 1020. In some embodiments, a permanent magnet without circuit connections to the stimulator 514 can be used for the same purpose and in the same fashion as a magnetic induction coil 1020 for locating cap 1000 (and by extension locating connector 530). In various embodiments of the present technology, either of, or both of, the induction coil 1020 (implantable) or the location module 1010 can be energized; and either can be the detected coil. For clarity, the present technology can provide a primarily two-dimensional (2D) location of the cap, e.g., the position on an implant recipient's skin closest to the cap. In other embodiments, the location module can provide information relating to the depth of the connector, for example, by the magnitude of magnetic coupling.

Figure 11:
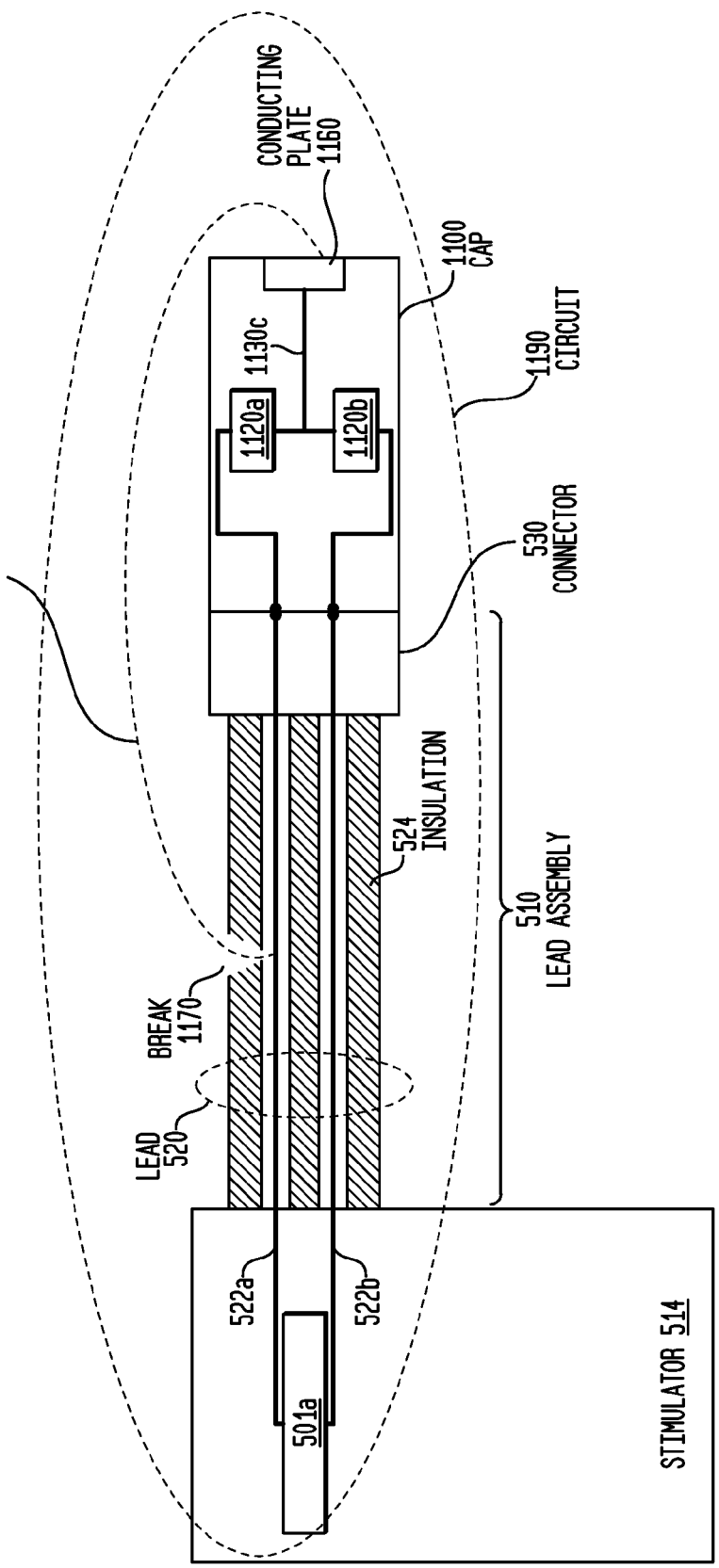
FIG. 11 is a schematic view of embodiments of a cap of the present technology, including a conductive plate, in relation to the implanted component and connector lead assembly of FIG. 5.

FIG. 11 is a schematic view of embodiments of a cap 1100 of the present technology, containing a conductive plate 1160 and circuit elements 1120a, 1120b in relation to the stimulator 514 and connector lead assembly 510 of FIG. 5. Conductive plate 1160 is in electrical communication with each of circuit elements 1120a and 1120b via conductive pathway 1130c. A break 1170 in insulation 524, such as a scalpel cut to the lead, is shown in FIG. 10 that exposes conductive pathway 522a to bodily fluids, thereby creating undesirable conductive pathway 1180.

Without the break 1170, circuit 1190 should provide a response characterized by circuit elements 1120a and 1120b in series. With the break 1170, the electrical impedance presented by circuit element 1120a will be in parallel with the electrical impedance presented by undesirable conductive pathway 1180 through conductive plate 1160, thereby changing the response of circuit 1190. Making the electrical impedance of circuit element 1120a different than the electrical impedance of circuit element 1120b allows an asymmetric break in the insulation 524 to be identified. In some embodiments, a single circuit element can be used in combination with a conductive plate or electrode exposed to the surface of the cap.

As with the embodiments illustrated in FIG. 8 and FIG. 9, the embodiments illustrated in FIG. 11 can be used to test for open and short circuits in a manner consistent with the electrical impedance characteristics of circuit elements 1120a and 1120b, along with being used to determine the location of the cap 1100 where at least one circuit element has electromagnetic characteristics that allow it to be located by a location module 810. In addition, an electromagnetic link between a location module 810 and the cap 1100 can allow data communication between the location module and the cap—and by extension between the location module and the stimulator 514. Such a communication channel can find use as a backup to the communication link between the external coil 130 and the internal coil 136, described in connection with FIG. 1.

Figure 12:
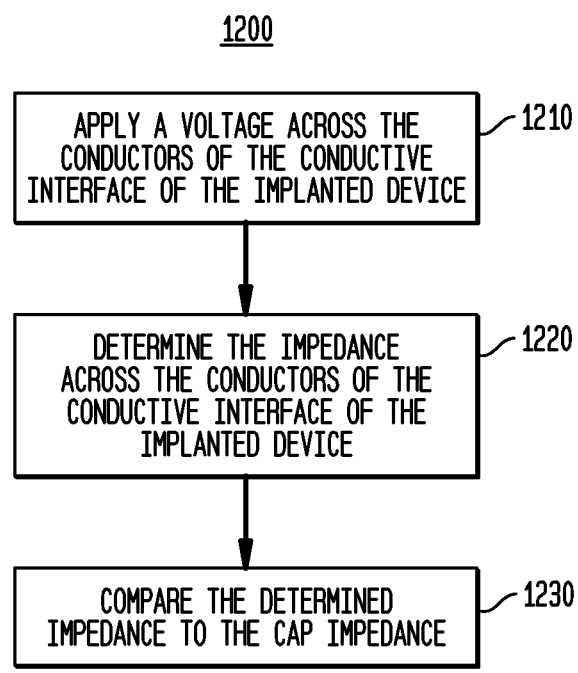
FIG. 12 illustrates methods of assessing the integrity of a connector lead assembly of an implanted device that is terminated with a cap in accordance with the present technology.

Referring to FIG. 12, methods 1200 of assessing the integrity of a connector lead assembly of an implanted device that is terminated with a cap in accordance with the present technology are shown. The cap includes an electrical impedance connected across conductive pathways of the connector lead assembly. In the methods a voltage is applied across conductive pathways of the connector lead assembly at the implanted device 1210. The electrical impedance across the conductive pathways of the connector lead assembly is determined 1220. The determined electrical impedance is compared to the cap electrical impedance 1230. A difference between the determined electrical impedance and the cap electrical impedance above a threshold value is an indication that the connector lead assembly has not maintained its integrity since implantation.

More generally, where an electrical connector lead assembly of an implanted device is terminated in a cap of the present technology including a circuit element as described above, the following method can be employed to assess the integrity of the implanted electrical connector lead assembly. A voltage can be applied across conductive pathways of the electrical connector lead assembly. A characteristic, e.g., impedance, of the network formed by the lead assembly conductive pathways and the cap can be measured. The measured characteristic can be compared to the expected characteristic of the network, e.g., for a lead assembly with negligible impedance, such characteristic is the known impedance of the cap circuit element. If the measured characteristic is with an acceptable range of the expected characteristic, then the integrity of the lead assembly has been confirmed. If not, then depending on the type of network in the cap, other conclusions can be drawn, e.g., as described above in connection with FIG. 7-FIG. 12.

Figure 13:
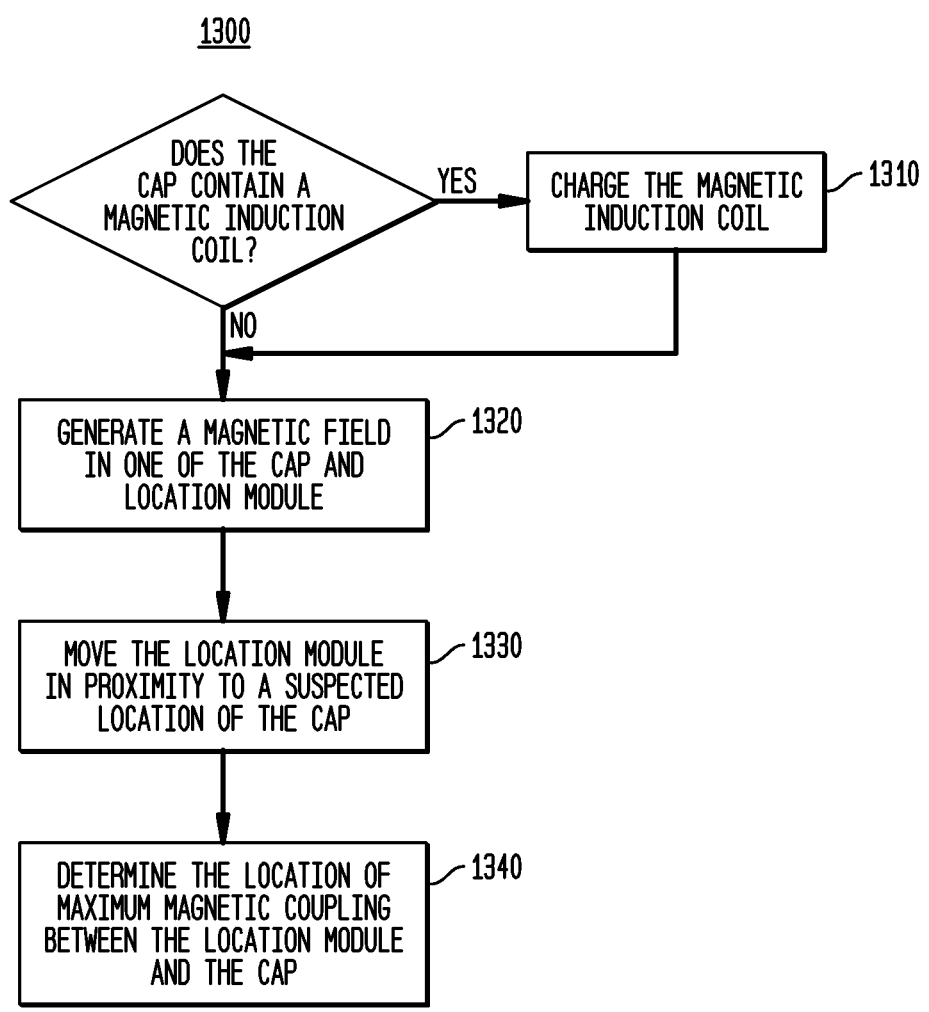
FIG. 13 illustrates methods of locating a connector lead assembly of an implanted device that is terminated with a cap in accordance with the present technology.

Referring to FIG. 13, methods 1300 of locating a connector lead assembly of an implanted device that is terminated with a cap in accordance with the present technology are shown. The cap includes at least one of: a natural magnet and a magnetic induction coil. In the methods, if the cap includes a magnetic induction coil, the magnetic induction coil is energized 1310. A magnetic field is generated in at least one of: the cap and the location module 1320, then the location module is moved in proximity to a suspected location of the cap 1330. The location of the cap is determined as under the location of maximum magnetic coupling between the location module and the cap 1340.

Figure 14:
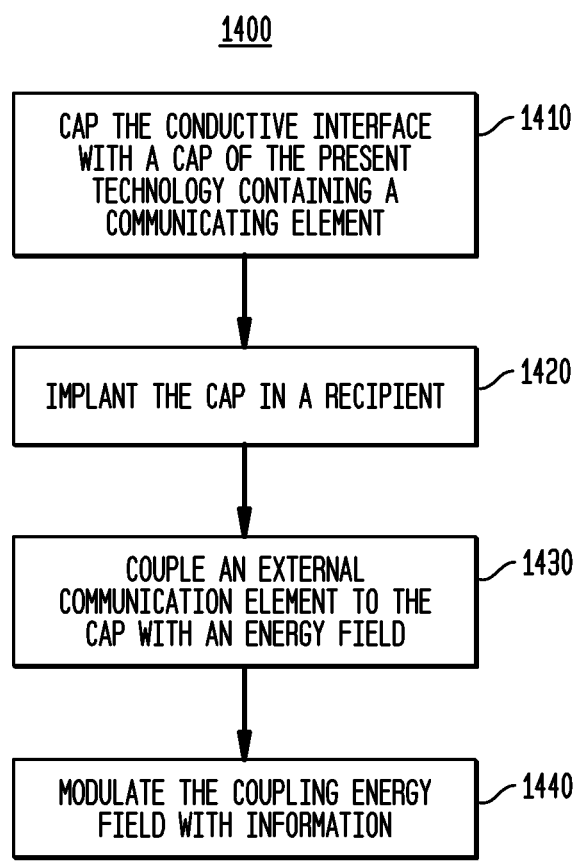
FIG. 14 illustrates methods for communicating with an implanted device having a connector lead assembly with a cap in accordance with embodiments of the present technology.

Referring to FIG. 14, methods 1400 for communicating with an implanted device having a connector lead assembly are illustrated. In such methods, the connector lead assembly is capped 1410 with a cap. The cap includes a body, at least one first contact, at least one second contact, a communicating circuit element, and at least two conductive pathways. The cap body includes a mating surface. The cap body is engageable with the connector lead assembly at the cap mating surface. Each contact disposed on the cap mating surface such that each contact conductively engages at least one corresponding connector lead assembly contact when the cap body is engaged with the connector lead assembly. A circuit is formed from a first contact to a second contact, and containing the communicating circuit element and at least two cap conductive pathways. The capped connector lead assembly can be implanted 1420 in a recipient. An external communication element is coupled to implanted device with an energy field 1430. The coupling energy field is modulated with information in at least one direction 1440. In some embodiments of the method, the energy field is a non-propagating magnetic field.

In some situations, a liquid material such as silicone may be used to coat at least the surface of the contacts of the connector lead assembly and the material may be allowed to cure in place. A sleeve may at least substantially surround the coating. Typically, removal of the sleeve and the coating from the connector lead assembly may be difficult to accomplished without risk of damaging the connector lead assembly; especially in the case of electrical joints.

Figure 15:
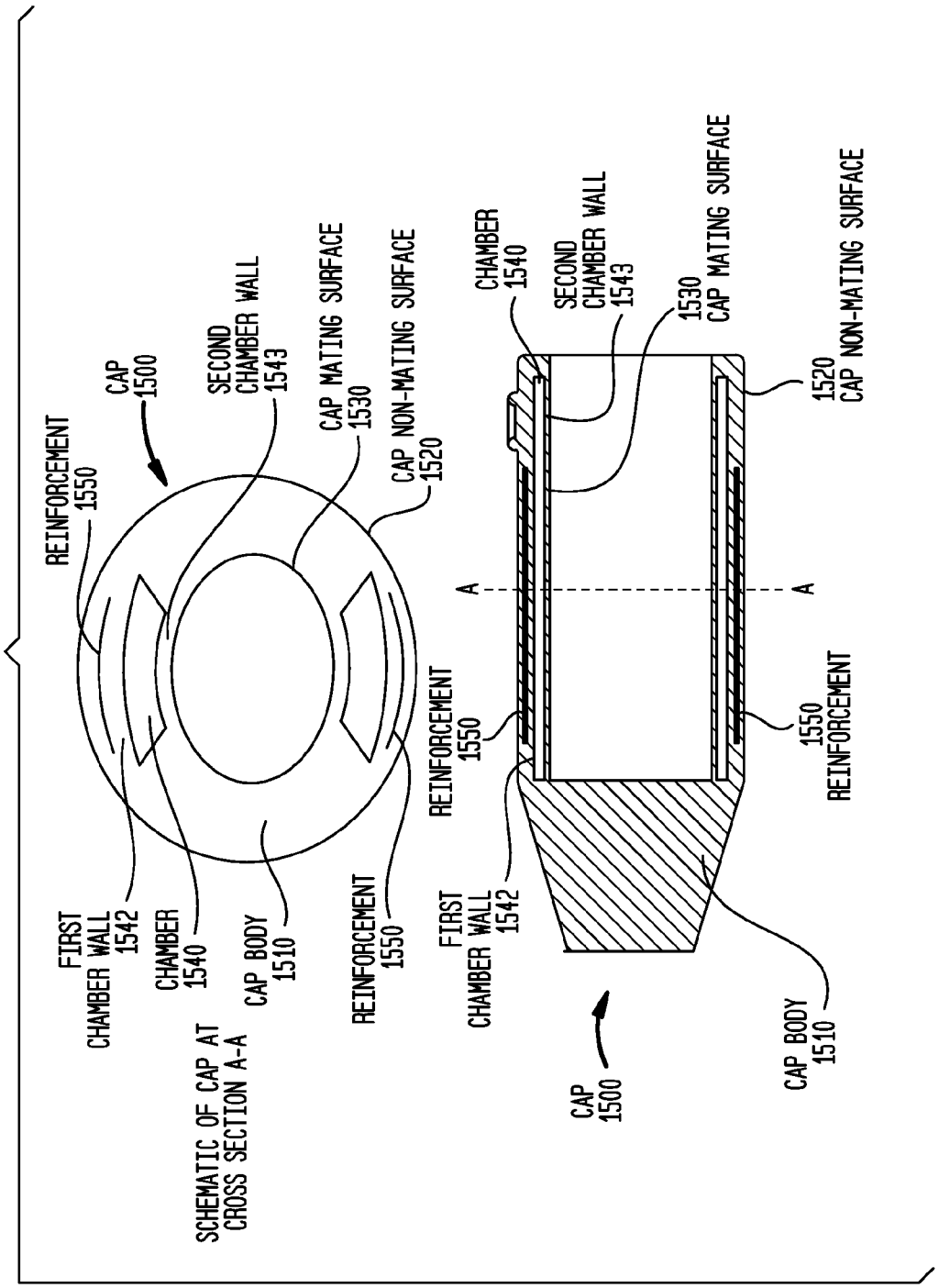
FIG. 15 illustrates a radial cross section and a longitudinal cross section of a cap in accordance with the present technology.

Some embodiments of the cap of the present technology include a chamber defined in the cap body between the cap mating surface and the cap non-mating surface. FIG. 15 shows a radial cross section and a longitudinal cross section of a cap 1500 of the present technology. The cap 1500 comprises a cap body 1510 generally defined by a cap non-mating surface 1520 and a cap mating surface 1530. The cap body 1510 can be made of silicone or polyurethane. The cap 1500 can include a drug-doped component as described in connection with cap 600.

The cap 1500 of FIG. 15 includes two chambers 1540, though caps in accordance with the present technology can include one, or three or more chambers. Each chamber 1540 can extend longitudinally along some or a majority of the length of the cap. While each chamber 1540 shown in FIG. 15 extends circumferentially through about 60 degrees, one or more chambers can extend around the full perimeter of the body 1510. Each chamber 1540 can be bounded by a first chamber wall 1542 forming a portion of the non-mating surface 1520, and a second chamber wall 1543 forming a portion of the mating surface 1530.

Both chamber walls 1542 and 1543 can have features that promote the electrical insulating protection of an implantable medical device connector lead assembly mated with the cap 1500. The second chamber wall 1543 of FIG. 15 can more distendable in comparison to the first chamber wall 1542, such that upon a chamber filling with a filler (such as filler 1660 of FIG. 16) the chamber will exert a sealing pressure on a portion of an implantable medical device connector lead assembly when mated with the cap 1500. The first chamber 1542 wall can be comparatively less distendable by being of the same material as, but thicker than, the second chamber wall 1543. The first chamber wall 1542 can be strengthened to resist distention by a reinforcement such as reinforcement 1550. The first chamber wall 1542 can be made from a material of greater durometer than the second wall 1543 to make it less distendable.

Figure 16:
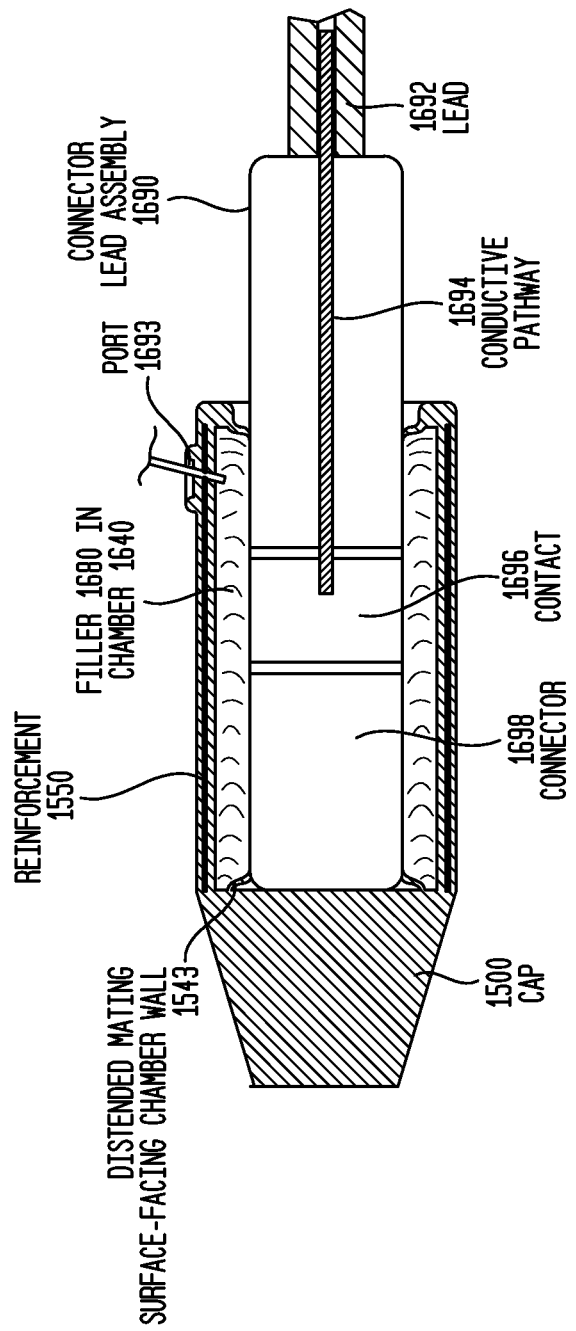
FIG. 16 illustrates a cap in accordance the present technology mating to a connector lead assembly of an implantable medical device.

Referring to FIG. 16, cap 1500 is shown mating with a connector lead assembly 1690 of an implantable medical device. The connector lead assembly comprises a lead 1692 and a conductive pathway 1694 connected to a contact 1696 disposed in a connector 1698. A filler 1680 can be introduced into the chamber 1640, for example upon manufacturing of the cap 1500, or through port 1693 at surgery after the cap 1500 is placed over the connector lead assembly 1690. Pressure from the filler 1680 can cause the more distendable second chamber wall 1543 to distend, thus promoting an electrically insulating seal around the portion of the connector lead assembly 1690 mated to the cap 1500. In the case of FIG. 16, contact 1696 is electrically sealed by at least partially filling at least one chamber 1540.

Filler 1680 can be a biocompatible liquid selected from the group consisting of saline or liquid silicone which may be cured in situ. A silicone can be a single-material filler, or a two-component filler, which when mixed, begins curing. A slit (not shown) may be created in the port 1693 to facilitate access, e.g., through use of a blunt needle. It is not necessary to have a filling port, particularly of a self-curing filler is used.

While various embodiments of the present technology have been described above, it should be understood that they have been presented by way of example only, and not limitation. For instance, while FIG. 1 illustrates a context of the present technology in which cochlear implant 100 includes an external component 142, it would be appreciated that in alternative embodiments, cochlear implant 100 may be a mostly-implantable or totally implantable medical device. For instance, embodiments of the cap technology described herein as interfacing with connector lead assembly 510 can also be used as interfacing with a connector directly on the body of the IMD. It will be apparent to persons skilled in the relevant art that various changes in form and detail can be made therein without departing from the spirit and scope of the technology. For instance, features described as part of one implementation can be used on another implementation to yield a still further implementation. Thus, the breadth and scope of the present technology should not be limited by any of the above-described exemplary embodiments, but should be defined only in accordance with the following claims and their equivalents.

What is claimed is:

1. A cap for protecting an electrical connector lead assembly of an implantable medical device, the cap comprising:
   a body having (1) a mating surface configured to receive at least a portion of the electrical conductor lead assembly of the implantable medical device and to electrically insulate a plurality of contacts of the electrical conductor lead assembly of the implantable medical device and (2) a non-mating surface; and
   an electrical network disposed within the body, wherein the electrical network comprises at least one of an electrical impedance, a magnetic induction coil, a resistor, a capacitor, an inductor, an open circuit tester, a conductive plate conductively exposed to an exterior of the cap.

2. The cap of claim 1 further comprising:
   a removal feature, to facilitate removal of the cap from the electrical connector lead assembly.

3. The cap of claim 2, wherein:
   the removal feature comprises at least one of a flap, a weakened region of the body, and a filament embedded in the body.

4. The cap of claim 1, wherein:
   the mating surface defines an elongate volume for receiving the portion of the connector lead assembly.

5. The cap of claim 2, wherein the cap further comprises:
   a reinforcing element surrounding at least portion of the cap.

6. The cap of claim 1, wherein the electrical network further comprises:
   first and second contacts exposed at the mating surface, a first circuit element, and
   two conductive pathways connecting the contacts to the circuit element;
   wherein the body is configured to mate with the electrical connector lead assembly such that each contact conductively engages a corresponding contact of the electrical connector lead assembly when the cap and electrical connector lead assembly are mated.

7. The cap of claim 6, wherein the first circuit element comprises:
   the electrical impedance.

8. The cap of claim 6, wherein the first circuit element comprises:
   the magnetic induction coil.

9. The cap of claim 6, wherein the circuit element comprises at least one of:
   the resistor, the capacitor, and the inductor.

10. The cap of claim 6, wherein the cap further comprises:
    a second circuit element series connected to the first circuit element; and
    the conductive plate, wherein the conductive plate is electrically connected to a conductive pathway between the series-connected circuit elements.

11. The cap of claim 1, wherein the electrical network comprises the open circuit tester.

12. The cap of claim 1 wherein:
    the body has defined therein a chamber between the mating surface and the non-mating surface;
    the chamber is bounded by:
    a first chamber wall forming a portion of the non-mating surface, and
    a second chamber wall forming a portion of the mating surface; and
    wherein the second chamber wall is distendable in comparison to the first chamber wall.

13. The cap of claim 12 wherein the chamber extends circumferentially around the body.

14. The cap of claim 12 further comprising:
    a reinforcement in the body between the first chamber wall and the non-mating surface.

15. The cap of claim 12 further comprising:
    a filler in the chamber.

16. An apparatus comprising:
    a cap comprising:
    a cap body comprising an inner surface and an outer surface; wherein the inner surface comprises a distendable wall and is configured to receive and electrically insulate at least one contact of an lead assembly; and
    an electrical network disposed in the cap body, wherein when the lead assembly is received in the inner surface, the electrical network is in communication with the at least one contact.

17. The apparatus of claim 16, wherein the electrical network comprises an open circuit tester.

18. The apparatus of claim 16, wherein the electrical network comprises:
    a first circuit element and a second circuit element connected in a series to the first circuit element; and a conductive plate conductively exposed on the outer surface and electrically connected to the first circuit element and the second circuit element.

19. The apparatus of claim 16, wherein the inner surface is configured to distend when the lead assembly is received in the cap body.

20. An apparatus comprising:
a cap comprising:
a cap body comprising an inner surface and an outer surface; wherein the inner surface is configured to receive and electrically insulate at least one contact of an lead assembly; and
an electrical network disposed in the cap body, wherein when the lead assembly is received in the inner surface, and wherein the electrical network is in communication with the at least one contact, and wherein the electrical network comprises at least one of an electrical impedance, a magnetic induction coil, a resistor, a capacitor, an inductor, an open circuit tester, an a conductive plate conductively exposed to an exterior of the cap.

21. The cap of claim 20, wherein the electrical network comprises the electrical impedance.

22. The cap of claim 20, wherein the electrical network comprises the magnetic induction coil.

23. The cap of claim 20, wherein the electrical network comprises at least one of:
the resistor, the capacitor, and the inductor.

24. The cap of claim 20, wherein the cap further comprises the conductive plate.

25. The cap of claim 20, wherein the electrical network comprises the open circuit tester.

* * * * *